United States Patent
Dupree et al.

(10) Patent No.: US 7,563,453 B2
(45) Date of Patent: Jul. 21, 2009

(54) COMPOSITIONS FOR CONTROLLED RELEASE OF PEST CONTROL PRODUCTS IN AQUATIC ENVIRONMENTS

(75) Inventors: Robert Dupree, Fergus (CA); Barrington M. J. Tyler, Ancaster (CA)

(73) Assignee: Pestalto Environmental Products, Guelph (CA)

( * ) Notice: Subject to any disclaimer, the term of this patent is extended or adjusted under 35 U.S.C. 154(b) by 382 days.

(21) Appl. No.: 10/543,388

(22) PCT Filed: Jan. 29, 2004

(86) PCT No.: PCT/CA2004/000121

§ 371 (c)(1), (2), (4) Date: Feb. 13, 2006

(87) PCT Pub. No.: WO2004/066728

PCT Pub. Date: Aug. 12, 2004

(65) Prior Publication Data

US 2006/0234867 A1    Oct. 19, 2006

Related U.S. Application Data

(60) Provisional application No. 60/443,164, filed on Jan. 29, 2003.

(51) Int. Cl.
*A01N 25/00* (2006.01)
*A01N 25/08* (2006.01)
*A01N 25/34* (2006.01)
*A01N 47/28* (2006.01)

(52) U.S. Cl. ............ 424/405; 424/408; 424/457; 514/594; 514/785

(58) Field of Classification Search ............ 424/405; 514/594
See application file for complete search history.

(56) References Cited

U.S. PATENT DOCUMENTS 4,631,857 A    12/1986    Kase et al.

FOREIGN PATENT DOCUMENTS

| WO | 9534200 | | 12/1995 |
|---|---|---|---|
| WO | WO 95/34200 | * | 12/1995 |
| WO | 9707675 | | 3/1997 |
| WO | 02087342 | | 11/2002 |

* cited by examiner

*Primary Examiner*—John Pak
*Assistant Examiner*—Nathan W Schlientz
(74) *Attorney, Agent, or Firm*—Patricia Folkins; Bereskin & Parr LLP/S.E.N.C.R.L., s.r.l.

(57) ABSTRACT

The present invention relates to compositions and methods for the controlled-release of pest control products into aquatic environments. The compositions comprise one or more pest control products in admixture with one or more water soluble and one or more water insoluble waxes. The compositions of the present invention are particularly useful for treating columns of water in catch basins.

7 Claims, No Drawings

COMPOSITIONS FOR CONTROLLED RELEASE OF PEST CONTROL PRODUCTS IN AQUATIC ENVIRONMENTS

This application is a 371 of PCT/CA04/00121, filed on 29 Jan. 2004.

FIELD OF THE INVENTION

The present invention is in the field of pest control products. In particular, the present invention relates to compositions for the controlled release of pesticides into aquatic environments.

BACKGROUND OF THE INVENTION

Pest control products developed to control the larval stages (larvicide) of nuisance insect pests are available in several different formulations such as wettable powders, granules, liquids etc. Although said products could be used for controlling nuisance larvae in confined areas such as catch basins, mixing and or weighing of the products would be necessary to deliver the required and correct dose. This process is laborious and not conducive to rapid treatment of numerous catch basins in a given time.

It is desirable to have the larvicide released to the environment in a controlled manner over a period of time thus providing the dose required to cause mortality and reducing the requirement for retreatment. The release rate of the larvicide to a water column can be controlled by the rate at which the carrier materials dissolve in the water column. Thus the selection and mixture of the carrier materials will determine the length of time for which control of nuisance insect larvae is achieved.

Controlled release compositions for treating a population of aquatic organisms in a column of water are disclosed in several U.S. patents issued to Levy, R. (see for example U.S. Pat. Nos. RE37,890, 6,391,328, 6,387,386, 6,350,461, 6,346,262, 6,337,078, 6,335,027, 6,001,382, 5,902,596, 5,885,605, 5,858,386, 5,858,384, 5,846,553 and 5,698,210). Levy describes compositions comprising a pesticide active agent, a carrier component and a coating component. Levy also suggests that the compositions may comprise only a pesticide active agent and a joint-function coating/carrier component. The only materials mentioned as being suitable as a joint-function coating/carrier component in Levy's compositions are polyvinyl alcohol, polyethylene oxide, hydroxypropyl methyl cellulose, cetyl alcohol and stearyl alcohol.

Another controlled release composition for the delivery of pesticides into an aquatic environment is described in Kase, L. E. et al. (Canadian Patent No. 1,225,023). The compositions therein comprise the active agent, a plurality of cork granules and molding plaster. The composition is designed to have a specific gravity of less than 1 so that it will float on the surface of the water.

Solid pesticide compositions in which the pesticide is dispersed in wax are described in U.S. Patents issued to Paulson, P. (see U.S. Pat. Nos. 5,750,128 and 5,505,019). The wax is typically made up of 1-30% microcrystalline wax, 5-40% paraffin oil and 60-95% paraffin wax and 10-25% of flour and/or starch is required to promote the dispersion of the pesticide into the wax. The compositions described in Paulson are designed for the application of pesticides to plants.

Timed released delivery systems in which the treating agent is encapsulated in a biodegradable wax are described in Harvan, D. J. et al. (U.S. Pat. No. 6,004,572). These systems are designed for the application of treating agents to wood and biodegradable waxes suitable for this purpose are microcrystalline waxes having a chain of 20 or more carbon atoms.

There is a need in the art for improved controlled release compositions for the effective delivery of pesticides to aquatic environments.

SUMMARY OF THE INVENTION

The present invention relates to compositions for the controlled release of pest control products into an aquatic environment. The carrier, which regulates the controlled release of the pest control product, is a blend of water-soluble and water-insoluble waxes. The release rate of the pest control product into the water can be controlled by the rate at which the carrier materials dissolve in the water.

Accordingly, the present invention relates to a composition for the controlled release of pest control products into an aquatic environment comprising one or more pest control products, one or more water soluble waxes and one or more water insoluble waxes.

The present invention further relates to an article of manufacture comprising a pest control composition of the present invention. The present invention also relates to an article of manufacture comprising a composition of the present invention, a cord having a first end and a second end, and a weight, wherein the composition of the present invention is molded around the first end of the cord and the weight is attached to the second end of the cord, said cord being of a length to allow the composition to be suspended in an aquatic environment.

The article may be dispensed conveniently into catch basins and may be of a size and shape such that the catch basin grill cover need not be removed for placement. The article can also be molded in different shapes, sizes and weights to be used in other water bodies to insure adequate concentration of the pest control product.

The present invention also relates to a method of treating an aquatic environment that may be infested with a pest or is expected to become infested with a pest comprising the administering an effective amount of a composition of the present invention to said aquatic environment.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

It is desirable to have a pest control product released to an aquatic environment in a controlled manner over a period of time thus providing the dose required to cause mortality and reduce the requirement for retreatment. The release rate of pest control product to water can be controlled by the rate at which the carrier materials dissolve in the water. Thus the selection and mixture of the carrier materials will determine the length of time for which control of pests is achieved.

The present invention relates to the use of a mixture of water soluble and water insoluble waxes as the carrier material for pest control products in aquatic environments. Accordingly, the present invention involves a composition for the controlled release of pest control products into an aquatic environment comprising one or more pest control products, one or more water soluble waxes and one dr more water insoluble waxes.

The one or more water soluble waxes and one or more water insoluble waxes may be any such waxes that will blend with each other and not separate once combined and solidified. The one or more water soluble waxes may be, for example, selected from one or more of water soluble modified ester waxes based on montan waxes, water soluble core waxes used in lost wax casting processes, water soluble waxes that are used in casting internal cavities which then dissolve when immersed in water, water soluble waxes used in cosmetics and as food additives and water soluble waxes which are of a solid state at temperatures ranging from 0-35° C. The one or more water insoluble waxes may be any water insoluble wax which will not separate upon solidification when combined with the one or more water soluble waxes. For example, when the water soluble wax is one or more of water soluble modified ester waxes based on montan waxes, the water insoluble wax may be a water insoluble modified ester waxes based on montan waxes. Examples of waxes include those identified by the trade names Licowax™ KSL (water insoluble), Licowax™ KST (water soluble), SOL-MAR-G™ (water soluble) and SOLU-GLO™ (water soluble) or any equivalent wax or wax type products with the same or similar chemical properties of these products. In embodiments of the present invention the one or more water soluble and water insoluble waxes comprises a mixture of Licowax™ KSL and Licowax™ KST. Mixtures of the two waxes can have a ratio ranging from 99:1 to 1:99 for Licowax KSL and Licowax KST respectively. The higher the ratio of Licowax KST the more rapidly the present invention will be solubilized in aqueous media and thus the higher the concentration of pest control product that will be delivered into the receiving environment per unit time. In an embodiment of the invention, the ratio of water insoluble wax to water soluble wax is about 3:2.

The one or more pest control products may be selected from any suitable pesticide, including chemicals or other materials including biological pesticides or control agents such as *Bacillus thuringiensis, Bacillus sphaericus* or viral agents or formulated products containing chemicals or other micro-organisms having pesticidal activity. In embodiments of the invention, the pest control product is a larvicide, i.e. it controls the larval stages of nuisance pests. In further embodiments of the invention, the nuisance pests are mosquitoes, or other such insect pests which may be found in an aquatic environment.

By aquatic environment it is meant any body of water including, for example, catch basins, ponds, lakes, bays, wetlands, marshes, swamps, tidal basins, lagoons, storm water retention ponds, sounds, creeks, streams, rivers, oceans, ditches, swales, sewage treatment systems, potholes, tree holes, rock holes, bromeliads and tires. Thus, the treated column of water can be either moving or stationary, and have any water quality that can be utilized as a habitat for the target organism(s).

The controlled release compositions of the present invention may also be combined with other formulating materials or ingredients or components wherein such components are diluents, adjuvants, dyes, alcohols, acetone, ketones, oils, surfactants, water, emulsifiers, film-forming agents, compatibility agents, wetting agents, salt, natural or synthetic polymers, hydrocolloids, buoyancy modifiers, ultraviolet absorbers, photo-protecting agents, suspending agents, elastomers, penetrants, deflocculating agents, dispersing agents, stabilizing agents, antifoaming agents, sticking agents, solvents, co-solvents, catalysts, or synergists, and the like, and combinations thereof, such as the two, three or four component combinations. Such ingredients are well known to those skilled in the art. The compositions of the present invention do not require an external coating component although they may be inserted into various shaped, disposable or reusable, degradable or non-degradable dispensing devices.

The present invention further relates to an article of manufacture comprising a pest control composition of the present invention. The article may be dispensed conveniently into aquatic environments and may be of any size and shape to suit specific environment to be treated. For example, when the aquatic environment is a catch basin, the article may be molded into a size and shape such that the catch basin grill cover need not be removed for placement. The article can also be molded in different shapes, sizes and weights to be used in other water bodies to insure adequate concentration of the pest control product.

In one embodiment of the present invention the aquatic environment is a catch basin. What is desired for delivering a pest control product to the unique conditions of a catch basin is a device that has a premeasured dose of pest control product based on the catch basin volume and that can be quickly and easily delivered to the catch basin. Such a device may also remain suspended in the water column but not float at the surface where it would be susceptible to being flushed out of the catch basin during a heavy rain event. Suspension in the water column also eliminates the problem of the device being buried in organic debris contained at the bottom of the catch basin, which can cause the pest control product to be made biologically unavailable if it is prone to binding with organic material. For this purpose, the compositions of the present invention may be molded around a cord of variable length to which a weight has been affixed to the opposite end. The composition acts as a carrier for a pest control product which permits the slow release of the pest control product over a predetermined period of time. The weighted end of the dispenser will sink to the bottom of the water and the opposite end, to which the mixture of waxes has been molded, will float in the water. The design of this article provides a convenient vehicle for the treatment of catch basins and other bodies of water wherein nuisance insect larvae develop.

Accordingly, the present invention further relates to an article of manufacture comprising a composition of the present invention, a cord having a first end and a second end, and a weight, wherein the composition of the present invention is molded around the first end of the cord and the weight is attached to the second end of the cord, said cord being of a length to allow the composition to be suspended in an aquatic environment.

A person skilled in the art would appreciate that the cord may be of any suitable material that has no appreciable solubility in water. The weight may also be of any suitable material that has no appreciable solubility in water. The weight must sink to the bottom of the aquatic environment and therefore must have a specific gravity greater than 1.

The article of manufacture may further comprise various shaped, disposable or reusable, degradable or non-degradable dispensing devices into which the compositions of the present invention may be inserted.

The composition comprising water soluble and water insoluble waxes can be blended such that the rate of solubilization is controlled to allow for the slow release of the one or more pest control products into the environment. The molding of the article may be achieved by delivering the one or more water soluble and water insoluble waxes, which are heated to a set temperature and is in a liquid state, and into which the one or more pest control products have been blended to achieve homogeneity, to a mold of predetermined size and shape. The mold may be filled to the desired level, for example, by an automated mechanical filling device and cooled with a coolant to cause solidification as rapidly as possible. The cord to which the article may be affixed, after solidification has occurred, may be drawn through the mold on a continuous basis via a hole of correct dimension at the bottom of the mold. Cord may be wrapped on spools to facilitate feeding of cord through the bottom of the mold. Once solidification has occurred the article may be removed from the mold by a mechanical arm, which grabs the cord protruding from the top of the mold, the mold may open by pneumatic actuators, the arm raises removing the article and which may now be transferred to a bin. During this process the mold may close by pneumatic actuators and may be refilled to the desired level. The process of filling the mold, cooling of the mold, removal of the article from the mold and refilling the mold may occur on a continuous basis and may be achieved using equipment that is automated.

The present invention also relates to a method of treating an aquatic environment that may be infested with a pest, or is expected to become infested with a pest, comprising administering an effective amount of a composition of the present invention to said aquatic environment.

The term "an effective amount" of an agent as used herein is that amount sufficient to effect beneficial or desired results and, as such, an "effective amount" depends upon the context in which it is being applied. For example, in the context of administering an agent for treating an environment that may be infested with a pest or is expected to become infested with a pest, an effective amount of an agent is, for example, an amount sufficient to achieve a reduction in the amount of said pest in the environment as compared to the response obtained without administration of the agent.

As used herein, and as well understood in the art, "treating" or "treatment" is an approach for obtaining beneficial or desired results. Beneficial or desired results can include, but are not limited to, decreasing the numbers of pests in the environment, decreasing or diminishing the size of the infestation, stabilizing (i.e. not worsening) state of infestation, preventing spread of pest infestation, delay or slowing of infestation progression, and remission (whether partial or total), whether detectable or undetectable, of infestation.

The compositions may be administered to the environment in any convenient manner. The amount or dosage of pest control agent will depend on size of the environment. The compositions may be administered with a frequency, and using any known method, until the desired reduction in the amount of pests is achieved.

The following non-limiting examples are illustrative of the present invention:

EXAMPLES

Development of the Controlled Release Formulation

Experiments were conducted to develop a controlled release formulation which would disperse over a given period of time. For the purposes of this experiment the desired period of time was 120 days.

Samples for experimentation were prepared which consisted of ratios of the ester modified montan waxes Licowax KSL and Licowax KST as follows:

| Licowax KSL % | Licowax KST % |
|---|---|
| 100 | 0 |
| 75 | 25 |
| 50 | 50 |
| 25 | 75 |
| 0 | 100 |

The waxes were heated to their respective melting points and then blended and mixed in the aforementioned ratios, and poured into a cylindrical mold of ½ inch diameter and 3 inches in length. Upon cooling and solidification each controlled release device (CRD) weighed 15 grams. Four CRDs for each aforementioned ratio of waxes was prepared.

The CRDs were then submersed into test containers that held 50 liters of water at 10° C. Visual observations were made and results recorded at 1, 2, 3, 4, 8, 16, 32 and 64 days to assess how rapidly the CRDs began to disintegrate and disperse within the test containers. Results indicated that CRDs composed of 100% Licowax KST dissolved rapidly within the test containers (i.e. <24 hours) and CRDs composed of 100% Licowax KSL showed no evidence of disintegration even after a period in excess of 60 days. Other CRDs disintegrated at rates which reflected their composition with those containing a higher ratio of the Licowax KST breaking down more rapidly. From this experiment it was concluded that the optimal composition to produce a CRD that would slowly disintegrate over a period of 120 days would comprise of a ratio of about 40% Licowax KST and about 60% Licowax KSL.

Addition of Active Ingredient to the Controlled Release Device

Additional experiments were conducted to assess whether a known active ingredient that is toxic to mosquito larvae could be blended with the CRD and still be efficacious. The active ingredient novaluron [Tradename: Rimon Technical (99% active ingredient), Makhteshim Agan of North America Inc.] was selected for these experiments. Novaluron is an insect growth regulator that interferes with the synthesis of chitin and causes mortality to insect larvae when maturing into an adult. Insect larvae will go through several growth stages known as instars. At each instar the outer integument is shed to allow for increase in body size. Novaluron disrupts this process causing death. It was determined that using 0.008 g of novaluron per CRD when placed into a test vessel containing 6 liters of water should provide a concentration within the water column to cause >95% mortality.

Methods

A mosquito colony of *Aedes aegypti* was established prior to commencement of the efficacy experiment in order to have mosquito larvae available on a continuous basis. *Ae. aegypti* eggs were obtained from a commercial supplier and reared to adults which were then housed in a plexiglass enclosure and provided with a synthetic carbohydrate source consisting of sugar dissolved in water, resting surfaces and brown paper toweling rolled and inserted into a jar filled with water. The moist brown paper toweling was provided as a substrate on which adult females could lay eggs. Upon emergence of adult female mosquitoes a source for bloodmeals was provided. Approximately 10 days following the administering of the bloodmeal the paper toweling now had eggs laid on it and was collected, replaced with new toweling and allowed to dry. This process was repeated several times prior to initiation of the efficacy experiment to insure an adequate supply of eggs was available.

Collected eggs were placed in a container with untreated tap water at ambient temperature, approximately 20° C., that had also been allowed to stand for 24 hours so any chlorine present in the water could disperse into the atmosphere. Hatching commenced within 12 hours and larvae were given commercial liver powder as a food source.

Preparation of CRDS containing Rimon Technical

CRDs were prepared using the method described above. Quantities of Licowax KST and Licowax KSL sufficient to prepare 4 CRDs weighing 15 grams each were heated and blended together in a glass beaker. Once the wax was molten and blended, 0.032 g of novaluron was carefully added and stirred into the blended wax. The beaker was then placed into a hot water bath at 95° C. for ½ hour to reheat the blended wax to reduce viscosity. After ½ hour it was restirred and then poured into molds as described previously and allowed to solidify. Molds were placed on a tarred scale prior to filing to insure that 15 g+/−0.01 grams of blended wax were added to each mold.

Test Vessels

Stainless steel test vessels with dimensions of 50 cm×29 cm×10 cm were filled with 6 liters of untreated tap water. The water surface area was 0.138 $m^2$. Vessels were topped up with tap water as required over the duration of the experiment to maintain a volume of 6 liters within each test vessel.

Test vessels were arranged in 3 rows of 4, with each row representing a replicate. Treatments were an untreated check, a positive control using Altosid Pellets containing the active ingredient methoprene and the CRDs blended with 0.008 g each. Test vessels were labeled indicating treatment and novaluron replicate and then randomized in each row. A ½ teaspoon of liver powder to provide a food source for the mosquito larvae was added to each test vessel.

The CRDs and Altosid Pellets were added to the test vessels 7 days prior to the addition of mosquito larvae. This was done to allow time for the CRDs and Altosid Pellets to begin dispersing in the water column of the test vessel. Fifty mosquito larvae ranging in size from 1st to 2nd instar were added to each test vessel. Dead larvae were counted and removed from each test vessel using an eye dropper at 1, 5, 7, 8 and 11 days after introduction.

Observations 1 day after introduction of mosquito larvae into the test vessels containing the CRDs, 100% mortality was observed in all replicates, 0% mortality in the Altosid Pellets and 0% mortality in the check. On day 12 (ie. 12 days after introduction of the CRD), 50 larvae were again reintroduced to the test vessels containing the CRDs. These larvae were in their $3^{rd}$ and $4^{th}$ instar stage of development. By day 18 (ie. 6 days after introduction of the $3^{rd}$ and $4^{th}$ instar larvae) the $3^{rd}$ and $4^{th}$ instar larvae had mortality ranging from 92-95%. By day 18 the larvae in the check had completed their development to adults with 0% mortality. By day 18 all larvae in the positive control containing Altosid Pellets had developed to the pupal stage and then were unsuccessful in emerging as adults, which is consistent with the mode of action of this product. See Table 1 for results.

Following the completion of this first trial a second trial was initiated where again 50 $1^{st}$ and $2^{nd}$ instar larvae were introduced into the test vessels containing the CRDs and the checks. The CRDs originally added to the test vessels during the first trial were not removed and since the initiation of the first trial had now been in the test vessels for a period of 32 days. Water was added as required to compensate for evaporation. Dead larvae were counted and removed. The positive control containing Altosid Pellets was eliminated from the experiment at this point. By day 39 (ie.7 days after introduction of the mosquito larvae) mortality ranged from 58-76%. By day 41 (ie. 9 days after introduction of the mosquito larvae) 100% mortality was observed in all replicates. No mortality was observed in any of the check replicates. See Table 2.

A third trial was initiated where again 50 $1^{st}$ and $2^{nd}$ instar mosquito larvae were added to each test vessel. The CRDS had now been in the test vessels for a period of 109 days. Water was added as required to compensate for evaporation. Dead larvae were counted and removed. By day 113 (i.e. 4 days after introduction of the mosquito larvae) mortality ranged from 80-100%. By day 117 (ie. 8 days after introduction of the mosquito larvae) mortality ranged from 98-100%. The check replicates were observed until day 120 by which time all had pupated or emerged as adults. The experiment was terminated on day 120. See Table 3.

CONCLUSIONS

The experiment performed under laboratory conditions demonstrated that the ingredients in the CRD did not inhibit the toxicity of the active ingredient novaluron to mosquito larvae. The quantity of novaluron (i.e. 0.008 g) used in the CRD was sufficient to cause mosquito larvae mortality of 98-100% up to 120 days after introduction into the test vessels.

Examples of a Formulation

| | |
|---|---|
| Licowax KSL | 6 g |
| Licowax KST | 9 g |
| novaluron | 0.008 g |

Formulation for invention as described above will cause mortality to mosquito larvae found in a container such as a catch-basin with a surface area of 0.636$m^2$ for a period of 45-120 days.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

First Trial

MORTALITY %

| Date<br>Days After Treatment | Apr. 25, 2003<br>0 DAT | May 1, 2003<br>7 DAT | May 2, 2003<br>8 DAT | May 6, 2003<br>12 DAT | May 8, 2003<br>14 DAT | May 9, 2003<br>15 DAT | May 12, 2003<br>18 DAT |
|---|---|---|---|---|---|---|---|
| Novaluron (0.008 g) | CRD added | larvae added | | Re-introduced larvae 3rd 4th instar | | | |
| Rep1 | to test | 50 | 100% | 50 | 6-8% | 54% | 92% |
| Rep2 | vessels | 50 | 100% | 50 | 3-5% | 46% | 95% |
| Rep3 | | 50 | 100% | 50 | 6-8% | 50% | 92% |
| Rep4 | | 50 | 100% | 50 | 6-8% | 46% | 94% |
| Altosid Pellets (0.35 g) | | | | | | | |
| Rep1 | | 50 | 0% | 85% | 95% | no data | 100% |
| Rep2 | | 50 | 0% | 65% | 85% | no data | 100% |
| Rep3 | | 50 | 0% | 65% | 80% | no data | 100% |
| Rep4 | | 50 | 5% | 75% | 95% | no data | 100% |
| Check (untreated) | | | | | | complete adult emergence | |
| Rep1 | | 50 | 0% | 0% | 0% | 0% | 0% |
| Rep2 | | 50 | 0% | 0% | 0% | 0% | 0% |
| Rep3 | | 50 | 0% | 0% | 0% | 0% | 0% |
| Rep4 | | 50 | 0% | 0% | 0% | 0% | 0% |

TABLE 2

Second Trial

MORTALITY %

| Days After Treatment | May 26, 2003<br>32 DAT | Jun. 2, 2003<br>39 DAT | Jun. 3, 2003<br>40 DAT | Jun. 4, 2003<br>41 DAT |
|---|---|---|---|---|
| with CRD Novaluron (0.008 g) | 50 larvae added | | | |
| Rep1 | 0% | 74% | 100% | |
| Rep2 | 0% | 58% | 98% | 100% |
| Rep3 | 0% | 66% | 96% | 100% |
| Rep4 | 0% | 76% | 98% | 100% |
| Check (untreated) | | | | trial ended |
| Rep1 | 0% | 0% | 0% | 0% |
| Rep2 | 0% | 0% | 0% | 0% |
| Rep3 | 0% | 0% | 0% | 0% |
| Rep4 | 0% | 0% | 0% | 0% |

TABLE 3

Third Trial

MORTALITY %

| Date<br>Days After Treatment | Aug. 11, 2003<br>109 DAT | Aug. 12, 2003<br>110 DAT | Aug. 15, 2003<br>113 DAT | Aug. 19, 2003<br>117 DAT | Aug. 21, 2003<br>119 DAT | Aug. 22, 2003<br>120 DAT |
|---|---|---|---|---|---|---|
| with CRD Novaluron (0.008 g) | 50 larvae added | | | | | |
| Rep1 | 0% | 0% | 80% | 100% | | |
| Rep2 | 0% | 0% | 80% | 98% | | |
| Rep3 | 0% | 0% | 95% | 99% | | |
| Rep4 | 0% | 0% | 100% | 100% | | |
| Check (untreated) | | | | | | |
| Rep1 | 0% | 0% | 0% | 0% | 92% pupae | 100% pupae |
| Rep2 | 0% | 0% | 0% | 0% | 30% pupae | 56% pupae |
| Rep3 | 0% | 0% | 0% | 0% | 24% pupae | 48% pupae |
| Rep4 | 0% | 0% | 0% | 0% | 6% pupae | 26% pupae |

We claim:

1. A composition for the controlled release of pest control products into a body of water comprising one or more mosquito larvicides, one or more water soluble modified ester waxes based on montan waxes and one or more water insoluble modified ester waxes based on montan waxes, wherein the weight ratio of water insoluble wax to water soluble wax is about 3:2; wherein said composition is prepared by heating the one or more water soluble waxes and the one or more water insoluble waxes to their respective melting points and then blending and mixing them in said weight ratio, into which the one or more mosquito larvicides is blended to achieve homogeneity, which is then delivered to a mold to provide the composition.

2. The composition according to claim 1, wherein the body of water is selected from the group consisting of catch basins, ponds, lakes, bays, wetlands, marshes, swamps, tidal basins, lagoons, storm water retention ponds, sounds, creeks, streams, rivers, oceans, ditches, swales, sewage treatment systems, potholes, tree holes, rock holes, bromeliads and tires.

3. The composition according to claim 2, wherein the body of water is a catch basin.

4. The composition according to claim 1, further comprising other formulating components, wherein such components are selected from the group consisting of diluents, adjuvants, dyes, alcohols, acetone, ketones, oils, surfactants, water, emulsifiers, film-forming agents, compatibility agents, wetting agents, salt, natural or synthetic polymers, hydrocolloids, buoyancy modifiers, ultraviolet absorbers, photo-protecting agents, suspending agents, elastomers, penetrants, deflocculating agents, dispersing agents, stabilizing agents, antifoaming agents, sticking agents, solvents, co-solvents, catalysts, synergists, and combinations thereof.

5. The composition according to claim 1, said composition not requiring an external coating component.

6. The composition according to claim 1, wherein the mosquito larvicide is novaluron.

7. A method of treating a body of water that may be infested with mosquitoes, or is expected to become infested with mosquitoes, comprising administering an effective amount of a composition according to claim 1 to said body of water.

* * * * *